US005994065A

United States Patent [19]

Van Ness

[11] Patent Number: 5,994,065
[45] Date of Patent: Nov. 30, 1999

[54] METHODS FOR PREPARING SOLID SUPPORTS FOR HYBRIDIZATION AND REDUCING NON-SPECIFIC BACKGROUND

[75] Inventor: Jeffrey Van Ness, Seattle, Wash.

[73] Assignee: Rapigene, Inc., Bothell, Wash.

[21] Appl. No.: 08/733,671

[22] Filed: Oct. 17, 1996

Related U.S. Application Data

[60] Provisional application No. 60/006,501, Oct. 18, 1995.

[51] Int. Cl.[6] ...................... C12Q 1/68

[52] U.S. Cl. ...................... 435/6; 435/4; 436/501; 935/77; 935/78

[58] Field of Search ...................... 435/4, 5, 6, 810; 436/501; 935/77, 78

[56] References Cited

FOREIGN PATENT DOCUMENTS

| | | |
|---|---|---|
| 221 308 A1 | 5/1987 | European Pat. Off. . |
| WO 92/03579 | 3/1992 | WIPO . |
| WO 94/00600 | 1/1994 | WIPO . |

OTHER PUBLICATIONS

Van Ness et al., "A versatile solid support system for oligodeoxynucleotide probe–based hybridization assays," *Nucleic Acid Research* 19(12): 3345–3350, 1991.

Bresser et al. (1983) Proceedings of the National Academy of Sciences, USA, vol. 80, pp. 6523–6527.

*Organic Chemistry* (published by Allyn and Bacon, Inc., Boston, Massachasetts, 1973, authors Morrison and Boyd), pp. 658–670.

Bresser et al., DNA, vol. 2, No. 3, pp. 243–254, 1983.

*Primary Examiner*—Ardin H. Marschel
*Attorney, Agent, or Firm*—Seed and Berry LLP

[57] ABSTRACT

Methods related to solid supports for binding reactions are disclosed. The present invention provides procedures for prepaing solid supports, and their use in binding assays, such that non-specific background on the solid supports is reduced. The reduction of non-specific background permits the detection of low levels of specific binding which normally would be masked by the non-specific binding. The methods are applicable to a variety of target ligands and probes, including nucleic acids such as oligonucleotides.

33 Claims, No Drawings

METHODS FOR PREPARING SOLID SUPPORTS FOR HYBRIDIZATION AND REDUCING NON-SPECIFIC BACKGROUND

CROSS-REFERENCE TO RELATED APPLICATION

This application claims the benefit of U.S. Provisional Application No. 60/006,501, filed Oct. 18, 1995, now abandoned.

TECHNICAL FIELD

The present invention is generally directed toward methods for preparing solid supports for use in hybridization reactions. This invention is more particularly related to procedures for preparing hybridization solid supports such that non-specific background is reduced by chemical treatment of the supports.

BACKGROUND OF THE INVENTION

Hybridization technology is a powerful tool to identify pairs of molecules with a complementary relationship to one another. Such technology has been applied to a variety of types of molecules, including nucleic acids and proteins. For example, nucleic acid hybridization is a well-known and documented method for identifying specific nucleic acid sequences. Nucleic acid hybridization is based on the base pairing of complementary nucleic acid strands. When single stranded nucleic acids are incubated in appropriate buffers, complementary base sequence form double strand stable molecules. The presence or absence of such pairing may be detected by a number of different methods well known in the art. Most hybridization assays previously described involve multiple steps such as the hybridization techniques described by Dunn and Hassell in *Cell* 12:23 (1977).

The typical hybridization assay protocol for detecting a target nucleic acid in a complex population of nucleic acids can be generally described as follows. Target nucleic acids are separated by size on a gel matrix (electrophoresis), or are cloned and isolated, or sub-divided into pools, or are used in a complex population. The target nucleic acids are then transferred, or spotted, or otherwise immobilized onto a solid support, such as a nylon membrane or nitrocellulose membrane. (This "immobilization" can also be referred to as "arraying.") The immobilized nucleic acids are then subjected to a heating step or UV radiation which irreversibly immobilizes the nucleic acid. The membranes are then immersed in one or more of the traditional "blocking agents" which include Denhardt's reagent (Denhardt, *Biochem. Biophys. Res. Comm.* 23:641 (1966)), heparin (Singh and Jones, *Nucleic Acids Res.* 12:5627 (1984)), and non-fat dried milk (Jones et al., *Gene Anal. Tech.* 1:3 (1984)). Frequently, these reagents are used in combination with single-strand DNA and detergents such as sodium dodecyl sulfate (SDS). In the northern analysis of non-abundant sequences, or hybridizations using RNA probes, or single-copy Southern hybridizations, Denhardt's reagent is generally used with 0.5% SDS and 100 micrograms/ml of fragmented denatured DNA. (50× Denhardt's reagent consists of 1% w/v Ficoll (type 400, Pharmacia), 1% w/v polyvinylpyrrolidone, 1% w/v bovine serum albumin (Fraction 5).) Blocking agents are generally included in both the prehybridization step and hybridization steps when nitrocellulose is used. However, when nucleic acid is immobilized on nylon membranes, the blocking agents are generally omitted from the hybridization solution since high concentrations of protein interfere with the annealing of the probe to its target nucleic. The latter problem is particularly noticeable when short probes, such as oligonucleotides, are employed. The target nucleic acids are then typically probed with labelled "signal" nucleic acid under stringent hybridization conditions. Signal nucleic acids are then frequently detected by using a conjugated enzyme in which the conjugated enzyme possesses one member of a ligand pair. The signal nucleic acid contains the other member of the ligand pair. Unbound enzyme is then washed away and the membrane is immersed in a substrate solution. Signal is then detected by colorimetric means, by fluorescence or by chemiluminescence, depending on substrate type. In short form, the hybridization assay protocol can be summarized as follows: Target nucleic acid is immobilized on a solid support. The solid support is treated with blocking agents to prevent spurious binding (non-specific binding; also known as "background") of probes. The solid support is then probed and signal is detected by a variety of means.

The use of a blocking agent to reduce non-specific binding is essential for a number of reasons, including to be able to detect low levels of specific binding which would be masked by the non-specific binding if the latter is not blocked. Unfortunately, the use of traditional blocking agents, such as those described above, has never been a reproducible method. Although tomes have been written on the subject, it is virtually impossible to uniformly "block," for example, an 8 inch by 12 inch piece of nitrocellulose or nylon membrane using a combination or cocktail of blocking reagents composed of Ficoll (type 400, Pharmacia), polyvinylpyrrolidone, bovine serum albumin (Fraction 5, Sigma), fragmented single nucleic acid, milk products, etc. The methods of the present invention as described herein overcome this limitation of previous methods.

Due to the problems associated with the current approaches for reducing non-specific background in hybridization reactions, there is a need in the art for new methods. The present invention fulfills this need, and further provides other related advantages.

SUMMARY OF THE INVENTION

Briefly stated, the present invention provides methods for preparing hybridization solid supports and their use in hybridization reactions. In one aspect, the present invention provides a method for preparing hybridization solid supports that reduces non-specific background, comprising the steps of: (a) contacting a solid support for hybridization with a target ligand under conditions sufficient to immobilize the target ligand to the solid support; and (b) reacting the solid support containing immobilized target ligand with a compound under conditions sufficient to block non-specific sites, thereby producing a blocked solid support containing immobilized target ligand, the compound having the formula:

(I)

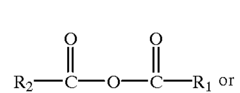

(II)

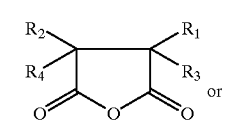

-continued

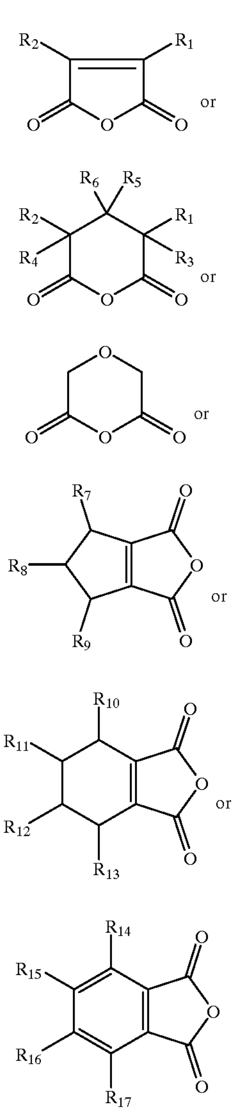

wherein $R_1$–$R_{17}$ are independently selected from H, OH, $CH_3$, $CH_2—CH_3$, $CH{=}CH—CH_3$, X, $CH_2X$, $CHX_2$, $CH_2—CH_2X$, $CH_2—CHX_2$, $CX_3$, $CX_2—CX_3$, $CX_2—CX_2—CX_3$ and $C({=}O)CH_3$, and $R_1$ and $R_3$, or $R_2$ and $R_4$, or $R_5$ and $R_6$ may be taken together as $=CH_2$, and $R_5$ and $R_6$ may be taken together as $=O$, and where each X is independently selected from halogen. In a preferred embodiment, the method additionally includes, after step (b), a step comprising eliminating substantially all of said compound that has not reacted with said blocked solid support containing immobilized target ligand. Also provided within the present invention are kits comprising a solid support, containing immobilized targeting ligand, prepared according to any of the above methods.

In another aspect, the present invention provides a method for reducing non-specific background in hybridization reactions, comprising the steps of: (a) contacting a solid support for hybridization with a target ligand under conditions sufficient to immobilize the target ligand to the solid support; (b) reacting the solid support containing immobilized target ligand with a compound under conditions sufficient to block non-specific sites, thereby producing a blocked solid support containing immobilized target ligand, the compound having the formula:

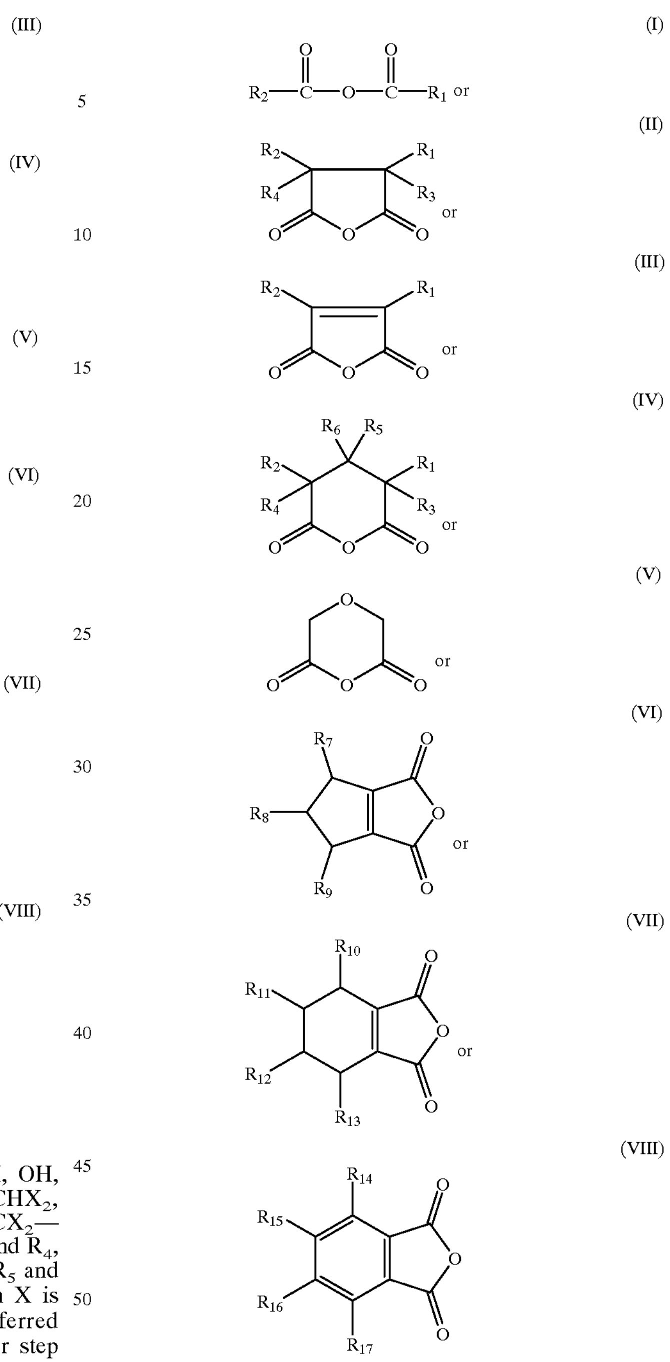

wherein $R_1$–$R_{17}$ are independently selected from H, OH, $CH_3$, $CH_2—CH_3$, $CH{=}CH—CH_3$, X, $CH_2X$, $CHX_2$, $CH_2—CH_2X$, $CH_2—CHX_2$, $CX_3$, $CX_2—CX_3$, $CX_2—CX_2—CX_3$ and $C({=}O)CH_3$, and $R_1$ and $R_3$, or $R_2$ and $R_4$, or $R_5$ and $R_6$ may be taken together as $=CH_2$, and $R_5$, and $R_6$ may be taken together as $=O$, and where each X is independently selected from halogen; (c) contacting the blocked solid support containing immobilized target ligand with a probe under conditions sufficient for specific binding to the immobilized target ligand; and (d) detecting the presence of the probe on the solid support, thereby determining hybridization between the target ligand and the probe. In a preferred embodiment, the method additionally includes, between steps (b) and (c), a step comprising eliminating substantially all of the compound that has not reacted with the blocked solid support containing immobilized target ligand. In another preferred embodiment, the method additionally includes, between steps (c) and (d), a step comprising eliminating substantially all of said probe that has not bound to said immobilized target ligand. In another preferred embodiment, the method additionally includes, between steps (b) and (c), a step comprising eliminating substantially all of the compound that has not reacted with the blocked solid support containing immobilized target ligand, and additionally includes, between steps (c) and (d), a step comprising eliminating substantially all of said probe that has not bound to said immobilized target ligand.

In preferred embodiments, the compound is according to formula I where $R_1$ and $R_2$ are both $CH{=}CH{-}CH_3$ or $CH_2X$ or $CX_3$ or $CX_2{-}CX_3$or $CX_2{-}CX_2{-}CX_3$, with each X independently selected from halogen. In other preferred embodiments, the compound is according to formula II where $R_1$–$R_4$ are H; or $R_1$ is $CH_3$ and $R_2$–$R_4$ are H; or $R_2$ and $R_4$ are H and $R_1$and $R_3$ are taken together as $=CH_2$; or $R_1$ and $R_2$ are H and $R_3$ and $R_4$ are $C(=O)CH_3$. In other preferred embodiments, the compound is according to formula III where $R_1$–$R_4$ are H; or $R_1$ is $CH_3$ and $R_2$ is H; or $R_1$ and $R_2$ are $CH_3$; or $R_1$ is X and $R_2$ is H; or $R_1$, and $R_2$ are X; with each X independently selected from halogen. In other preferred embodiments, the compound is according to formula IV where $R_1$–$R_6$ are H; or $R_1$–$R_5$ are H and $R_6$ is $CH_3$; or $R_1$ and $R_3$ are $CH_3$ and $R_2$, $R_4$, $R_5$ and $R_6$ are H; or $R_1$–$R_4$ are H and $R_5$ and $R_6$ are $CH_3$; or $R_1$–$R_4$ are H and $R_5$ is $CH_3$ and $R_6$ is $CH_2CH_3$; or $R_1$–$R_6$ are X; or $R_1$ and $R_2$ are H and $R_3$ and $R_4$ are $C(=O)CH_3$ and $R_5$ and $R_6$ are taken together as $=O$. In other preferred embodiments, the compound is according to formula VI where $R_7$–$R_9$ are H. In other preferred embodiments, the compound is according to formula VII where $R_{10}$–$R_{13}$ are H. In other preferred embodiments, the compound is according to formula VIII where $R_{14}$ and $R_{17}$ are X and $R_{15}$ and $R_{16}$ are H; or $R_{14}$–$R_{17}$ are X; or $R_{14}$ is OH and $R_{15}$–$R_{17}$ are H.

These and other aspects of the present invention will become evident upon reference to the following detailed description.

DETAILED DESCRIPTION OF THE INVENTION

As noted above, the use of traditional blocking agents has never been a reproducible method for uniformly blocking non-specific binding to hybridization solid supports. The methods of the present invention overcome this limitation of the prior art methods by achieving a uniform level of blocking of non-specific sites on hybridization solid supports, such as nitrocellulose or nylon membranes. The present invention represents a significant improvement in the hybridization field in that the reduction of non-specific background increases substantially the signal-to-noise ratio. This permits, for example, the replacement of radiolabelled probes with chemically labeled probes which are compatible with fluorescence or chemiluminescence signal systems. In addition, by eliminating the need for the traditional blocking agents, the present invention has the further advantages of lowering the risk of nuclease or protease contamination and lowering the cost of conducting large scale hybridizations.

Hybridization assays are useful to identify molecules that are capable of binding to a selected molecule. As used herein, the term "hybridization" refers to the specific binding between any two molecules and includes, for example, binding between two nucleic acid molecules. Such hybridization assays typically involve a series of steps which may be generally described as above. In short, a molecule (i.e., a target ligand) is immobilized on a solid support. The solid support is treated with a blocking agent(s) to decrease non-specific binding of a probe molecule. The solid support containing immobilized target molecule is probed with a candidate binding partner (i.e., a probe molecule). The presence or absence of the probe molecule bound to the solid support is detected, thereby determining whether hybridization between the target ligand and probe has occurred.

As noted above, prior to the step of probing, a solid support is prepared such that a target molecule is immobilized thereto and non-specific binding sites are blocked. A variety of solid supports may be used as the hybridization matrix within the present invention and are well known in the art. Any solid support capable of immobilizing a target ligand without significantly impairing its ability to bind a binding partner, is suitable. Solid supports possessing preactivated surfaces to immobilize a target ligand are well known to those in the art and are commercially available. Solid supports include both porous and non-porous solid supports. Porous solid supports include porous membranes. Examples of porous membranes include nitrocellulose membranes (e.g., Schleicher and Schuell, Keene, N.H.) and nylon membranes (e.g., Amersham, Arlington Heights, Ill., or Schleicher and Schuell, Keene, N.H.). Non-porous solid supports include microbeads, glass surfaces and fused silica. Examples of non-porous microbeads include magnetic beads, polystyrene, Teflon®, nylon, silica and latex. Magnetic beads can be obtained from PerSeptive Diagnostics (Cambridge, Mass.) or Dynal (Oslo, Noirway). Latex, silica and other types of beads can be obtained from Polysciences (Warrington, Pa.). Where the target ligand is a nucleic acid, particularly preferred solid supports are a nitrocellulose membrane, a nylon membrane or a glass surface. Where the target ligand is a protein, particularly preferred solid supports are a nitrocellulose membrane or a nylon membrane.

A target ligand is immobilized on a solid support such as those described above. A variety of molecules may be used as the target ligand within the present invention. Any molecule capable of immobilization on a solid support is suitable. Target ligands include nucleic acids, proteins and small organic or bio-organic (e.g., natural products) molecules. As used herein, the term "nucleic acid" includes deoxyribonucleic acid (DNA including genomic DNA and cDNA), ribonucleic acid (RNA including mRNA, rRNA and tRNA), oligonucleotides and nucleic acid analogs. As used herein, the term "protein" includes proteins (such as enzymes and antibodies), polypeptides, peptides (i.e., more than two amino acids), protein complexes and amino acid analogs. "Proteins" that are negatively charged are preferred protein target ligands. Target ligands may be obtained in a variety of ways including commercial sources, purification from biological sources, recombinant production and synthetic chemistry preparation.

Upon selection of a target ligand such as those described above, it is immobilized on a solid support. A variety of immobilization procedures may be used within the present invention and are well known to those in the art. Any immobilization procedure that deposits or attaches a target ligand without significantly impairing its ability to bind a binding partner, is suitable. Traditional means for immobilization a solid support include heat or UV irradiation. For immobilization by heating (e.g., baking under vacuum), temperatures typically range from about 50° to 100° C. for a period of about 1 minute to 60 minutes. For immobilization by irradiation, UV power typically ranges from about 1,000–1,000,000 microjoules/$cm^2$ for a period of about 10 seconds to 5 minutes. By subjecting a solid support in the presence of a targeting ligand to one of a variety of such reaction conditions, the targeting ligand is irreversibly immobilized on the solid support.

As noted above, the present invention provides a different procedure for blocking non-specific binding sites on solid supports prepared for use in hybridization reactions. Non-specific binding sites permit binding of a candidate binding partner (probe) to a solid support in a manner that is independent of the target ligand immobilized on the solid support. Non-specific binding of a probe to a solid support possessing immobilized target ligand gives the appearance that the probe is a binding partner to the target ligand. Within the present invention, following immobilization of a target ligand on a solid support, the solid support is reacted with one or more compounds such as those set forth below to block non-specific binding sites on the solid support. Compounds which may be used in the presents invention include the anhydrides depicted by the following formulae I–VIII:

(I)

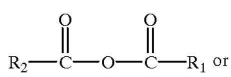

(II)

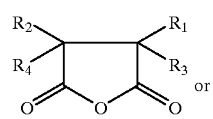

(III)

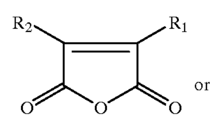

(IV)

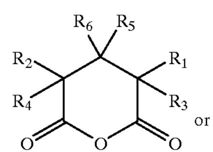

(V)

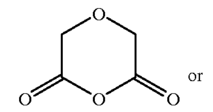

(VI)

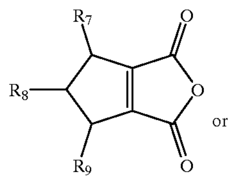

(VII)

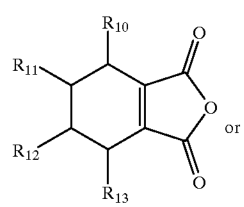

-continued (VIII)

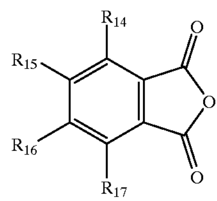

The compounds represented by formulae I–VIII possess substituents $R_1$ to $R_{17}$ as denoted above. Each of $R_1$ to $R_{17}$ is selected independently (i.e., the selection of one substituent may be made without regard for the selection of any other substituent) from substituents that include the following: H, OH, $CH_3$, $CH_2$—$CH_3$, CH═CH—$CH_3$, X, $CH_2X$, $CHX_2$, $CH_2$—$CH_2X$, $CH_2$—$CHX_2$, $CX_3$, $CX_2$—$CX_3$, $CX_2$—$CX_2$—$CX_3$ and C(═O)$CH_3$. Each "X" is independently selected from halogen, i.e., F, Cl, Br and I. In addition, substituents attached to the same ring carbon may be taken together as ═$CH_2$ or ═O. For example, any or all of $R_1$ and $R_3$, $R_2$ and $R_4$ or $R_5$ and $R_6$ may be taken together as ═$CH_2$. Similarly, for example, $R_5$ and $R_6$ may be taken together as ═O. A variety of anhydrides are commercially available (e.g., Aldrich, Milwaukee, Wis.) or may be synthesized using procedures known in the art (e.g., procedures described in March and references cited therein: J. March, *Advanced Organic Chemistry*, 2nd edition, McGraw-Hill, New York, N.Y. (1977)). It will be evident to those in the art when in possession of the present disclosure that variations on the above compounds are contemplated by, and may be used in, the practice of the present invention and are within the spirit and scope of the invention. A suitable compound is reacted with a solid support containing immobilized targeting ligand under conditions sufficient to block non-specific sites. Briefly, a compound is generally mixed with a solvent such as a polar solvent. The solution is added to the solid support for a time generally ranging from about several minutes to several hours at a temperature generally ranging from about room temperature to below the boiling point of the solvent. For example, succinic anhydride is mixed, to yield a final concentration of about 0.01 mg to 10 mg per ml, with a solvent such as m-pyrol, acetonitrile or other polar solvents, containing about 0.01 to 0.5 M sodium borate at a pH of about 7 to 9. The reaction with the solid support is allowed to proceed for about 2 to 60 minutes at a temperature of about 20° to 37° C. Where a particular targeting ligand may react with the compound and such reaction could significantly affect the targeting ligand's ability to bind a probe, it may be desirable to protect against such a reaction between the targeting ligand and the compound. This may be accomplished in a variety of ways, including protecting the targeting ligand or adjusting the conditions under which the compound is reacted with a solid support containing immobilized targeting ligand. For example, the pH may be adjusted to a pH which allows substantial reaction of the solid support with the compound, but does not permit substantial reaction of the targeting ligand with the compound. Alternatively, for example, functional groups on the targeting ligand that may be reactive with the compound may be reversibly protected. The targeting ligand is reacted with one or more protective chemicals that prevent reaction with the compound, and the protective groups are removed from the targeting ligand after the compound has been reacted with the solid support containing immobilized targeting ligand. Techniques for reversible protection of functional groups on molecules are known to those in the art (e.g., procedures described in Greene and references cited therein: T. W. Greene, *Protective Groups in Organic Synthesis*, John Wiley and Sons, New York, N.Y. (1981)).

As shown above, both non-aromatic and aromatic compounds may be used within the present invention. Examples of compounds include: propionic anhydride, butyric anhydride, isobutyric anhydride, valeric anhydride, (s)-(+)-methylbutyric anhydride, trimethylacetic anhydride, hexanoic anhydride, heptanoic anhydride, decanoic anhydride, lauric anhydride, palmitic anhydride, stearic anhydride, docosanoic anhydride, crotonic anhydride, methacrylic anhydride, oleic anhydride, linoleic anhydride, chloroacetic anhydride, iodoacetic anhydride, dichloroacetic anhydride, trifluoroacetic anhydride, chlorodifluoroacetic anhydride, trichloroacetic anhydride, succinic anhydrides, pentafluoropropionic anhydride, heptafluorobutyric anhydride, methylsuccinic anhydride, 2,2-dimethylsuccinic anyhydride, cis-1,2-cyclohexanedicarboxylic anhydride, trans-1,2-cyclohexanedicarboxylic anhydride, phthalic anhydrides, itaconic anhydride, 2-dodecen-1-ylsuccinic anhydride, dicarboxylic anhydrides, cis-aconic anhydride, s-acetylmercaptosuccinic anhydride, (+)-diacetyl-L-tartaric anhydride, maleic anhydrides, citraconic anhydride, 2,3-dimethylmaleic anhydride, maleic anhydrides, glutaric anhydrides, benzoic-, 2,3-diphenylmaleic-, 2-phenylglutaric-, homophalic-, isatoic-, N-methylisatoic-, 5-chloroisatoic-, phthalic-, 2-sulfobenzoic acid cyclic-, 4-methylphthalic-, 3,6-difluorophthalic-, 3,6-dichlorophthalic-, 4,5-dichlorophthalic-, tetrafluorophthalic-, tetrabromophthalic-, 3-hydroxyphthalic-, carboxylic-anhydrides, 3-nitrophthalic-, 4-nitrophthalic-, diphenic-, and naphalic-anhydrides.

Preferred compounds include: crotonic anhydride, chloroacetic anhydride, dichloroacetic anhydride, trifluoroacetic anhydride, chlorodifluoroacetic anhydride, trichloroacetic anhydride, pentafluoropropionic anhydride, heptafluorobutyric anhydride, succinic anhydride, methylsuccinic anhydride, 2,2-dimethylsuccinic anhydride, itaconic anhydride, maleic anhydride, citraconic anhydride, 2,3-dimelthylmaleic anhydride, 1-cyclopentene-1,2-dicarboxylic anhydride, 3,4,5,6-tetrahydrophthalic anhydride, bromomaleic anhydride, dichloromaleic anhydride, glutaric anhydride, 3-methylglutaric anhydride, 2,2-dimethylglutaric anhydride, 3,3-dimethylglutaric anhydride, 3-ethyl-3-methylglutaric anhydride, hexafluoroglutaric anhydride, 3,5-diacetyltetrahydropyran-2,4,6-trione, diglycolic anhydride, 3,6-difluorophthalic anhydride, 3,6-dichlorophthalic anhydride, tetrafluorophthalic anhydride, tetrachlorophthalic anhydride, tetrabromophthalic anhydride, 3-hydroxyphthalic anhydride, and 2,3-dibromomaleic anhydride.

Prior to use of a "blocked" solid support (containing a target ligand) in a hybridization reaction, it may be desirable to eliminate substantially all of the blocking compound that has not reacted with the solid support. A variety of ways may be used to perform this elimination within the context of the present invention. For example, unreacted compound may be washed out, such as by rinsing the solid support with a solution not containing the compound. Similarly, unreacted compound may be eliminated by physical removal of the solid support from the reaction solution. Alternatively, unreacted compound may be eliminated by a chemical quenching reaction. For example, unreacted anhydride may be converted to a non-reactive form by hydrolysis or reaction with an amine that is added to the reaction solution. Any of these techniques may be used with another or all in combination. The elimination of unreacted compound may be performed immediately after immobilization or after an intervening time period. If the time interval is sufficiently long, no action may be needed as the anhydride may have already hydrolyzed to a non-reactive form. Further, there may be situations where the presence of unreacted compound does not interfere with the particular use of a solid support containing immobilized targeting ligand.

Following preparation of a solid support containing immobilized targeting ligand and blocked non-specific sites, the solid support is contacted with a probe (candidate binding partner) to determine if the probe can hybridize with the targeting ligand. Any of the molecules described above for use as a targeting ligand may be used as a probe. Accordingly, probes include nucleic acids, proteins and small organic or bio-organic (e.g., natural products) molecules. For example, where the probes are nucleic acids, the nucleic acids may be obtained from the entire sequence or portions thereof of an organism's genome, from messenger RNA (mRNA) or from cDNA. Once the appropriate sequences are determined, DNA probes are preferably chemically synthesized using commercially available methods and equipment (e.g., Applied BioSystems, Foster City, Calif.). For example, the solid phase method can be used to produce short probes of between 15 and 50 bases (Caruthers et al., *Cold Spring Harbor Symp. Quant. Biol.* 47:411 (1982)).

The hybridization medium will generally contain standard buffers and detergents. A buffer such as sodium citrate, Tris HCl, PIPES or HEPES at a concentration of about 0.01 M to 0.2 M can be used. The hybridization medium will typically also contain about 0.01% to 0.5% of an ionic or nonionic detergent such as sodium dodecyl sulfate (SDS) or Sarkosyl (Sigma, St. Louis, Mo.), between about 1 to 10 mM EDTA, and about 0.1 to 1 M NaCl. Other additives may be included, such as volume exclusion agents which include a variety of polar water-soluble agents such as anionic polyacrylate, or polymethacrylate, and charged saccharidic polymers such as dextran sulfate and the like. The hybridization assays of the present invention can be performed by any method known to those in the art or analogous to immunoassay methodology given the guidelines presented herein. Hybridization assays are typically performed at temperatures ranging from about 4° C. to 70° C. for time periods which typically range from about 1 hour to 72 hours. Hybridization temperatures are known to be dependent on the concentrations of salts, chaotropes and the like present in solutions which support hybridizations. Preferred methods of assay are the sandwich assay and variations thereof, and the competition or displacement assay. Hybridization techniques are generally described in *Nucleic Acid Hybridization, A Practical Approach*, Hames and Higgins (eds.), IRL Press (1985); Gall and Pardue, *Proc. Natl. Acad. Sci. USA*. 63:378 (1969); and John etal., *Nature* 223:582 (1969). As improvements in hybridization are made, they can be readily applied.

The specificity (stringency) of hybridization (i.e., binding of probe to targeting ligand) may be controlled by a number of different ways known in the art (e.g., *Molecular Cloning: A Laboratory Manual*, Sambrook et al. (eds.), Cold Spring Harbor Press (1989)). For example, specificity may be controlled by varying the salt concentration, incubation time and/or incubation temperature. The control of specificity may be e xerted at the point of the binding reaction or at a wash step or at both. For example, the conditions in the incubation of a probe with a target ligand immobilized on a solid support may be such that only stringent binding is permissible. Alternatively, the conditions for the binding reaction may be less stringent, but a wash (following the binding reaction) may be under stringent conditions to control the specificity of any probe that remains bound to the solid support via the immobilized target ligand. Within the context of the present invention, the specificity of the binding of a probe to immobilized target ligand may be controlled in any of a variety of ways, including those described above.

For example, after hybridization at a temperature and time period appropriate for the particular hybridization solution used, a solid support to which the probe nucleic acid-target nucleic acid complex is attached is introduced into a solution typically containing similar reagents (e.g., NaCl, buffers, organic solvents, and detergents), as provided in the hybridization solutions. These reagents may be at similar concentrations as in the hybridization solutions, but often at lower concentration when high stringency in hybridization is required. The time period for washing may vary from about several minutes to several hours. Either the hybridization or the wash medium can be stringent. After appropriate stringent washing, the correct hybridization complex may now be detected in accordance with the nature of the label.

The determination of the extent of hybridization may be done by any of the methods well known in the art. If there is no detectable hybridization, then the extent of hybridization is zero. Hybridization may be detected "directly" (i.e., where the probe contains a reporter group) or "indirectly" (i.e., where the reporter group is on a molecule used to detect the presence of a probe). Various labels (signals) are suitable for use within the present invention. Labels act as reporter groups for detecting duplex formation between a target sequence and its complementary signal sequence. A reporter group as used herein is a group which has a physical or chemical characteristic which can be observed, measured or detected. Detectability may be provided by such characteristics as color change, luminescence, fluorescence, or radioactivity; or it may be provided by the ability of the reporter group to serve as a ligand recognition site. Typically, for example, labelled signal nucleic acid probes are used to detect nucleic acid hybridization. Complementary nucleic acids (signal probes) may be labelled by one of several methods typically used to detect the presence of hybridized polynucleotides. For example, labeled nucleic acid probes include double-strand DNA labelled by nick translation, single-strand DNA prepared by primer extension of an oligonucleotide annealed to a recombinant M13 bacteriophage, radiolabelled oligonucleotide probes or biotin or digoxin labelled synthetic oligonucleotide probes, or RNA synthesized in vitro with procaryotic DNA-dependent RNA polymerases (e.g., bacteriophage SP6, T 7, or T3 RNA polymerases). Methods to synthesize and use these probes are described, for example, in *Molecular Cloning, A Laboratory Manual*, Sambrook et al. (eds.), Cold Spring Harbor Press (1989). The most common method of detection is the use of autoradiography with $^{3}$H, $^{125}$I, $^{35}$S, $^{14}$C, $^{32}$P-labelled probes and the like. Other labels include ligands which bind to labelled antibodies, fluorophores, chemiluminescent agents, enzymes, and which can serve as specific binding pair members for a labelled ligand. It will be evident to those in the art that the choice of label depends on sensitivity requirements, ease of conjugation with the probe, stability requirements and availability requirements.

Non-isotopic probes may be labeled directly with signal (such as fluorophores, chemiluminescent agents, enzymes and enzyme substrates) or labeled indirectly by conjugation with a ligand capable of binding to a moiety having a detectable signal bound thereto. For example, biotin covalently bound to a probe can bind streptavidin that is bound covalently to a detectable signal, such as an enzyme or photoreactive compound. Ligand and receptor combinations may be widely varied. Where a ligand has a natural "receptor" (i.e., ligands such as biotin, thyroxine and cortisol), it may be used in conjunction with its labeled, naturally occurring receptor. Alternatively, a hapten or antigen may be used in combination with a suitably labeled antibody.

Non-radioactive probes are often labelled by indirect means. Generally a ligand molecule is covalently bound to the probe. The ligand then binds to an antiligand molecule which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with naturally occurring anti-ligands. Alternatively, any haptenic or antigenic compound can be used in conjunction with an antibody.

Enzymes suitable for use as signals include hydrolases (particularly phosphatases), esterases, ureases, glycosidases, oxidoreductases (particularly perioxidases). Suitable fluorescent signals include fluorescein and its derivatives, rhodamine and its derivatives, dansyl umbelliferone and the like. Chemiluminescers useful within the claimed invention include luciferin, luminol, and 1,2-dioxetanes.

The amount of labeled probe which is present in the hybridization solution may vary widely. Generally, substantial molar excesses of probe over the amount of target ligand will be employed in order to enhance the rate of the binding of the probe to the target ligand.

The means of detecting signal is determined by the signal selected. For example, where the label is a radioisotope, the support surface containing captured and labeled probe-target ligand complexes may be exposed to X-ray film or analyzed in a scintillation or gamma counter. Where the label is fluorescent, complexes are irradiated with light of a particular wavelength and is absorbed by the labeled complex, resulting in the emission of light of a lower wavelength which is detected. Where the label is an enzyme, complexes are incubated with an appropriate substrate for the enzyme, and the signal generated may be, for example, a colored precipitate, a colored or fluorescent soluble compound or material, or photons generated by bioluminescence or chemiluminescence.

The probe may be directly conjugated to the label. For example, where the probe is radioactive, the probe in association with its complement is exposed to X-ray film. Where the label is fluorescent, the sample is detected by first irradiating it with light of a particular wavelength and the emission is then picked up by a detector (Freifelder, *Physical Biochemistry*, W. H. Freeman & Co. (1982), p. 537). Where the label is an enzyme, the sample is detected by incubation on an appropriate substrate for the enzyme. The signal generated may be a colored precipitate, a colored or fluorescent soluble material or photons generated by bioluminescence or chemiluminescence. For example, alkaline phosphatase will dephosphorylate indoxyl phosphate which will then participate in a reduction reaction to convert tetrazolium salts to a highly colored and insoluble formazan.

The label may also allow the indirect detection of the hybridization complex. For example, where the label is a hapten or antigen, the sample can be detected by using antibodies. In these systems, a signal is generated by attaching fluorescent or enzyme molecules to an antibody, and in some cases, by attachment to a radioactive compound. (Tijssen, "Practice and Theory of Enzyme Immunoassays," *Laboratory Techniques in Biochemistry and Molecular Biology*, Burdon and van Knippenberg (eds.), Elsevier (1985), p. 9.)

Prior to detection of probe, it may be desirable to eliminate substantially all of the probe that has not bound to the immobilized target ligand. A variety of ways may be used to perform this elimination within the context of the present invention. For example, unbound probe may be washed out, such as by rinsing the solid support. Similarly, unbound probe may be eliminated by physical removal of the solid support from the hybridization reaction solution. Alternatively, unbound probe may be eliminated by a quenching reaction (i.e., unbound probe is converted to a form which is no longer detectable). Any of these techniques may be used with another or all in combination.

The following examples are offered by way of illustration and not by way of limitation.

EXAMPLES

Example 1

Demonstration of the Reduction of Background with Succinic Anhydride Blocked Nitrocellulose Compared to the Denhardt's Blocked Nitrocellulose Using a Colorimetric Reporter In this example, DNA is spotted on a nitrocellulose filter, immobilized, probed with a complementary biotinylated oligonucleotide. The hybridized signal oligonucleotide is then detected with streptavidin/alkaline phosphatase using a colorimetric substrate. The chemical means of blocking nitrocellulose is compared with traditional blocking agents.

Plastic-backed nitrocellulose (Schleicher and Schuell, part #76489, Keene, N.H.) was cut into 1×3 cm pieces. The nitrocellulose was then soaked briefly in 50% ethanol by immersing one end and pulling through the ethanol solution. The sheets were washed three times briefly in water and then soaked with shaking in 2×SSC (20×SSC is 175.3 g NaCl and 88.2 g sodium citrate dissolved in a final volume of 1 liter of water at pH 7.0) for 5 minutes. 100 ng of lamba double strand DNA (dsDNA) was spotted at 300 micron intervals. The DNA was irreversibly immobilized by UV irradiation (120,000 microjoules/cm$^2$ over a 30 second period). To denature the dsDNA, the sheets were wetted with 50% EtOH, and then washed 2× with water. The sheets were then soaked in denaturation solution (0.1 N NaOH, 0.05 mM EDTA) at room temperature for 1 minute, rinsed quickly with water, washed three times briefly in neutralization solution (0.1 M Tris pH 7.2, 0.05 mM EDTA), washed once in water and sheets patted dry with paper towels. The DNA was again treated with UV irradiation (120,000 microjoule,/cm$^2$ over a 30 second period). The sheets were rehydrated with 50% ethanol for 5 minutes, and washed twice with water.

The sheets were then split into 2 containers for separate "blocking" procedures. One container contained nitrocellulose sheets that were blocked with the chemical agent succinic anhydride. To block the sheets with succinic anhydride, 2.5 grams of succinic anhydride was dissolved in 25 ml m-pyrol and 125 ml 0.1 M NaBorate pH 8.5 was added. The solution was mixed well and then added to the sheets. Incubation with gentle mixing was for 10 minutes. The sheets were then washed 5 times with 0.01 M Tris, and 0.005 EDTA. The sheets in the second container were blocked with 5× Denhardt's solution. This was performed by placing 10 ml of 50× stock of Denhardt's solution (5 grams Ficoll (type 400, Pharmacia), 5 grams polyvinylpyrrolidone, 5 grams bovine serum albumin (Fraction 5, Sigma) and water to 500 ml total volume) into 90 ml water and adding fragmented single strand herring sperm DNA to a final concentration of 100 micrograms/ml. The solution was mixed well and then added to sheets. Incubation with gentle mixing for 30 minutes. The sheets were then washed 5 times with 0.01 M Tris pH, and 0.005 EDTA.

Biotinylated oligonucleotide (DMO 469; SEQ ID NO: 1 (GTTTAACATACTTTCATTT)) was added to a final concentration of 10 ng/ml in 1000 μl of rapid hybridization solution (Rapid-Hyb, Amersham, Arlington Heights, Ill.). The hybridizations were heated to 42° C. for 60 minutes. The sheets were then rinsed four times with 1×SSC/0.1% SDS for 1 minute per wash. The sheets were then washed 2× with Wash Solution (0.01 M Tris pH 7.2, 0.1 M NaCl, 0.005 M EDTA, 0.1% Sarkosyl.

The streptavidin/alkaline phosphatase conjugate (Vector, Burlingame, Calif.) was diluted (1:10,000) in wash solution. The solution was then applied to the sheets for 1 hour at room temperature with shaking. The sheets were then rinsed four times with wash solution, rinsed once with detection buffer (0.1 M NaCl, 0.01 M Tris pH 8.5, 0.05 M $MgCl_2$) for 5 minutes. The alkaline phosphatase substrate was prepared by dissolving a BCIP/NBT tablet (Schleicher and Schuell, part #78349, Keene, N.H.) in 30 mls $dH_20$. The reaction was carried out for 4 hours at room temperature. The sheets were then rinsed with water and dried.

TABLE 1

| | Succinic Anhydride Block | Denhardt's Block |
|---|---|---|
| Color of Background on a Scale of 1–10 | 1 | 7 |

The results (Table 1) indicated a significant lower level of "background" color on the sheets treated with succinic anhydride compared to the sheets blocked with Denhardt's reagent.

Example 2

Demonstration of the Reduction of Background with Succinic Anhydride Blocked Nitrocellulose Compared to the Denhardt's Blocked Nitrocellulose Using a Fluorescent Reporter In this example, DNA is spotted on a nitrocellulose filter, immobilized, probed with a complementary biotinylated oligonucleotide. The hybridized signal oligonucleotide is detected with streptavidin/alkaline phosphatase using 4-methyl-umbelliferyl phosphate (4-hydroxy-methyl coumarin). The chemical means of blocking nitrocellulose is compared with traditional blocking agents.

Plastic-backed nitrocellulose (Schleicher and Schuell, part #76489, Keene, N.H.) was cut into 1×3 cm pieces. The nitrocellulose was then soaked briefly in 50% ethanol by immersing one end and pulling through the ethanol solution. The sheets were washed three times briefly in water and then soaked with shaking in 2 ×SSC for 5 minutes. 100 ng of lamba double strand DNA was spotted at 300 micron intervals. The DNA was irreversibly immobilized by UV irradiation (120,000 microjoules/cm$^2$ over a 30 second period). To denature the dsDNA, the sheets were wetted with 50% EtOH, and then washed 2× with water. The sheets were then soaked in denaturation solution (0.1 N NaOH, 0.05 mM EDTA) at room temperature for 1 minute, rinsed quickly with water, washed three times briefly in neutralization solution (0.1 M Tris pH 7.2. 0.05 mM EDTA), washed once in water and sheets patted dry with paper towels. The DNA was again treated with UV irradiation (120,000 microjoules/$cm^2$ over a 30 second period). The sheets were rehydrated with 50% ethanol for 5 minutes, washed twice with water. The sheets containing DNA were marked differently than control sheets which contained no DNA.

The sheets were then split into 2 containers for separate "blocking" procedures. One container contained nitrocellulose sheets that were blocked with the chemical agent succinic anhydride. To block the sheets with succinic anhydride, 2.5 grams of succinic anhydride was dissolved in 25 ml m-pyrol and 125 ml 0.1 M NaBorate pH 8.5 was added. The solution was mixed well and then added to sheets. Incubation with gentle mixing was for 10 minutes. The sheets were then washed 5 times with 0.01 M Tris, and 0.005 EDTA. The sheets in the second container were blocked with 5× Denhardt's solution. This was performed by placing 10 ml of 50× stock of Denhardt's solution (5 grams Ficoll (type 400, Pharmacia), 5 grams polyvinylpyrrolidone, 5 grams bovine serum albumin (Fraction 5, Sigma) and water to 500 ml total volume) into 90 ml water and adding fragmented single strand herring sperm DNA to a final concentration of 100 micrograms/ml. The solution was mixed well and then added to sheets. Incubation with gentle mixing for 30 minutes. The sheets were then washed 5 times with 0.01 M Tris pH 7.2, and 0.005 EDTA.

Biotinylated oligonucleotide (DMO 469; SEQ ID NO: 1 (GTTTAACATACTTTCATTT)) was added to a final concentration of 10 ng/ml in 1000 μl of rapid hybridization solution (Rapid-Hyb, Amersham, Arlington Heights, Ill.). The hybridizations were heated to 42° C. for 60 minutes. The sheets were then rinsed four times with 1× SSC, 0.1% SDS for 1 minute per wash. The sheets were then washed 2× with Wash Solution (0.01 M Tris pH 7.2, 0.1 M NaCl, 0.005 M EDTA, 0.1% Sarkosyl.

The streptavidin/alkaline phosphatase conjugate (Vector, Burlingame Calif.) was diluted (1:10,000) in wash solution. The solution was then applied to the sheets for 1 hour at room temperature with shaking. The sheets were then rinsed four times with wash solution, rinsed once with detection buffer (0.1 M NaCl, 0.01 M Tris pH 8.5, 0.05 M $MgCl_2$,) for 5 minutes. The sheets were then individually incubated with 1 ml of 0.5 mM 4-methyl-umbelliferyl phosphate (4-hydroxy-methyl coumarin). The reaction was carried out for 4 hours at room temperature. Part of the solution was removed (150 microliters) and placed in a black microtiter plate (Dynatek Laboratories, Chantilly, Va.). The plates were then read directly using a Fluoroskan II fluorometer (Flow Laboratories, McLean, Va.) using an excitation wavelength of 360 nm and monitoring emission at 456 nm.

TABLE 2

| Sheet # | Succinic Anhydride Block | Denhardt's Block |
|---|---|---|
| +DNA | 425 rfu | 619 rfu |
| −DNA | 20 rfu | 395 rfu |

The results (Table 2) indicated a significant lower level of "background" color on the sheets treated with succinic anhydride compared to the sheets blocked with Denhardt's reagent.

Example 3

Demonstration of the Reduction of Background with Succinic Anhydride Blocked Nitrocellulose Compared to the Denhardt's Blocked Nitrocellulose Using a Chemiluminescent Reporter In this example, DNA is spotted on a nitrocellulose filter, immobilized, probed with a complementary biotinylated oligonucleotide. The hybridized signal oligonucleotide is detected with streptavidin/alkaline phosphatase and using the chemiluminescent substrate Lumingen. The chemical means of blocking nitrocellulose is compared with traditional blocking agents.

Plastic-backed nitrocellulose (Schleicher and Schuell, part #76489, Keene, N.H.) was cut into 1×3 cm pieces. The nitrocellulose was then soaked briefly in 50% ethanol by immersing one end and pulling through the ethanol solution. The sheets were washed three times briefly in water and then soaked with shaking in 2×SSC for 5 minutes. 100 ng of lamba double strand DNA was spotted at 300 micron intervals. The DNA was irreversibly immobilized by UV irradiation (120,000 microjoules/$cm^2$ over a 30 second period). To denature the dsDNA, the sheets were wetted with 50% EtOH, and then washed 2× with water. The sheets were then soaked in denaturation solution (0.1 N NaOH, 0.05 mM EDTA) at room temperature for 1 minute, rinsed quickly with water, washed three times briefly in neutralization solution (0.1 M Tris pH 7.2, 0.05 mM EDTA), washed once in water and sheets patted dry with paper towels. The DNA was again treated with UV irradiation (120,000 microjoules/$cm^2$ over a 30 second period). The sheets were rehydrated with 50% ethanol for 5 minutes, washed twice with water. The sheets containing DNA were marked differently than control sheets which contained no DNA.

The sheets were then split into 2 containers for separate "blocking" procedures. One container contained nitrocellulose sheets that were blocked with the chemical agent succinic anhydride. To block the sheets with succinic anhydride, 2.5 grams of succinic anhydride were dissolved in 25 ml m-pyrol and 125 ml 0.1 M NaBorate pH 8.5 was added. The solution was mixed well and then added to sheets. Incubation with gentle mixing was for 10 minutes. The sheets were then washed 5 times with 0.01 M Tris, and 0.005 EDTA. The sheets in the second container were blocked with 5× Detihardt's solution. This was performed by placing 10 ml of 50× stock of Denhardt's solution (5 grams Ficoll (type 400, Pharmacia), 5 grams polyvinylpyrrolidone, 5 grams bovine serum albumin (Fraction 5, Sigma) and water to 500 ml total volume) into 90 ml water and adding fragmented single strand herring sperm DNA to a final concentration of 100 micrograms/ml. The solution was mixed well and then added to the sheets. Incubation with gentle mixing for 30 minutes. The sheets were then washed 5 times with 0.01 M Tris pH 7.2, and 0.005 EDTA.

Biotinylated oligonucleotide (DMO 469; SEQ ID NO: 1 (GTTTAACATACTTTCATTT)) was added to a final concentration of 10 ng/ml in 1000 μl of rapid hybridization solution (Rapid-Hyb, Amersham, Arlington Heights, Ill.). The hybridizations were heated to 42° C. for 60 minutes. The sheets were then rinsed four times with 1× SSC, 0.1% SDS for 1 minute each wash. The sheets were then washed 2× with Wash Solution (0.01 M Tris pH 7.2, 0.1 M NaCl, 0.005 M EDTA, 0.1% Sarkosyl.

The streptavidin/alkaline phosphatase conjugate (Vector, Burlingame Calif.) was diluted 1:10,000) wash solution. The solution was then applied to sheet for 1 hour at room temperature with shaking. The sheets were then rinsed four times with wash solution, rinsed once with detection buffer (0.1 M NaCl, 0.01 M Tris pH 8.5, 0.05 M $MgCl_2$) for 5 minutes. The sheets were then individually incubated with 1 ml of Lumingen (Lumingen Inc., Detroit, Mich.). The reaction was carried out for 4 hours at room temperature. Part of the solution was removed (200 microliters) and placed in a 5 mm×40 mm polyporpylene tubes. Signal was measured using a Turner TD 20e luminometer (Turner Designs, Sunnyvale, Calif.) with an integration time of one minute.

TABLE 3

| Sheet # | Succinic Anhydride Block | Denhardt's Block |
|---|---|---|
| +DNA | 680 rfu | 725 rfu |
| −DNA | 200 rfu | 580 rfu |

The results (Table 3) indicated a significant lower level of "background" color on the sheets treated with succinic anhydride compared to the sheets blocked with Denhardt's reagent.

Example 4

Demonstration of the Reduction of Background with Both Nylon and Nitrocellulose Membranes Using Succinic Anhydride as the Blocking Agent (the presence of hybridized probe is detected using a colorimetric reporter)

In this example, DNA is immobilized on different filter types, probed with a complementary biotinylated oligonucleotide. The hybridized signal oligonucleotide is then detected with streptavidin/alkaline phosphatase using a colorimetric substrate. The chemical means of blocking nitrocellulose is compared with traditional blocking agents.

The membranes filters used in this example include Protran Nitrocellulose, plastic-backed nitrocellulose (part #76489), Optitran™ nitrocellulose, Nytran® nylon membrane (Schleicher and Schuell, Keene, N.H.) and Hybond™-N and Hybond™-N+ nylon membranes (Amersham. Arlington Heights, Ill., 60005)

Nitrocellulose and nylon membrane filters were cut into 1×1 cm pieces. The nitrocellulose was then soaked briefly in 50% ethanol by immersing one end and pulling through the ethanol solution. The sheets were washed three times briefly in water and then soaked with shaking in 2× SSC for 5 minutes. 100 ng of lamba double strand DNA was spotted at 300 micron intervals. The DNA was irreversibly immobilized by UV irradiation (120,000 microjoules/$cm^2$ over a 30 second period). To denature the dsDNA, the sheets were wetted with 50% EtOH, and then washed 2× with water. The sheets were then soaked in denaturation solution (0.1 N NaOH, 0.05 mM EDTA) at room temperature for 1 minute, rinsed quickly with water, washed three times briefly in neutralization solution (0.1 M Tris pH 7.2, 0.05 mM EDTA), washed once in water and sheets patted dry with paper towels. The DNA was again treated with UV irradiation (120,000 microjoules/$cm^2$ over a 30 second period). The sheets were rehydrated with 50% ethanol for 5 minutes, washed twice with water.

The sheets were then split into 2 containers for separate "blocking" procedures. One container contained nitrocellulose sheets that were blocked with the chemical agent succinic anhydride. To block the sheets with succinic anhydride, 2.5 grams of succinic anhydride was dissolved in 25 ml m-pyrol and 125 ml 0.1 m NaBorate pH 8.5 was added. The solution was mixed well and then added to the sheets. Incubation with gentle mixing was for 10 minutes. The sheets were then washed 5 times with 0.01 M Tris, and 0.005 EDTA. The sheets in the second container were blocked with 5× Denhardt's solution. This was prepared by placing 10 ml of 50× stock of Denhardt's solution (5 grams Ficoll (type 400, Pharmacia), 5 grams olyvinylpyrrolidone, 5 grams bovine serum albumin (Fraction 5, Sigma) and water to 500 ml total volume) into 90 ml water and adding fragmented single strand herring sperm DNA to a final concentration of 100 micrograms/ml. The solution was mixed well and then added to sheets. Incubation with gentle mixing for 30 minutes. The sheets were then washed 5 times with 0.01 M Tris pH, and 0.005 EDTA.

Biotinylated oligonucleotide (DMO 469; SEQ ID NO: 1 (GTTTAACATACTTTCATTT)) was added to a final concentration of 10 ng/ml in 1000 $\mu$l of rapid hybridization solution (Rapid-Hyb, Amersham, Arlington Heights, Ill.). The hybridizations were heated to 42° C. for 60 minutes. The sheets were then rinsed four times with 1× SSC/0.1% SDS for 1 minute per wash. The sheets were then washed 2× with Wash Solution (0.01 M Tris pH 7.2, 0.1 M NaCl, 0.005 M EDTA, 0.1% Tween 20).

The streptavidin/alkaline phosphatase conjugate (Vector, Burlingame Calif.) was diluted 1:10,000) wash solution. The solution was then applied to sheet for 1 hour at room temperature with shaking. The sheets were then rinsed four times with wash solution, rinsed once with detection buffer (0.1 M NaCl, 0.01 M Tris pH 8.5, 0.05 M MgCl2) for 5 minutes. The alkaline phosphatase substrate was prepared by dissolving a BCIP/NBT tablet (Schleicher and Schuell, part #78349, Keene, N.H.) in 30 mls $dH_20$. The reaction was carried out for 0.5 to 4 hours room temperature. The sheets were then rinsed with water and dried.

TABLE 4

| Membrane Type | Succinic Anhydride Block | Denhardt's Block |
|---|---|---|
| Protran Nitrocellulose | 1 | 3 |
| plastic-backed nitrocellulose | 1 | 6 |
| Optitran ™ nitrocellulose | 1 | 3 |
| Nytran ® nylon membrane | 1 | 4 |
| Hybond ™ -N nylon membrane | 1 | 4 |
| Hybond ™ -N+ nylon membrane | 1 | 5 |

where the intensity of the background is graded on a scale of 1 to 10 with 1 representing a nearly unchanged surface color (white) and 10 representing an intensely colored surface (dark brown).

The results (Table 4) indicated a significant lower level of "background" color on the sheets treated with succinic anhydride compared to the sheets blocked with Denhardt's reagent.

Example 5

Demonstration of the Reduction of Background with Propionic Anhydride, Butyric Anhydride, Difluorophthalic Anhydride Blocked Nitrocellulose Compared to the Denhardt's Blocked Nitrocellulose Using a Colorimetric Reporter In this example, three types of anhydrides are compared. To compare the type of anhydrides, DNA was spotted on a nitrocellulose filter, immobilized, and probed with a complementary biotinylated oligonucleotide. The hybridized signal oligonucleotide was then detected with streptavidin/horseradish peroxidase (SA/HRP) using a colorimetric substrate (4-methoxy-napthol, 4 MN). The chemical means of blocking nitrocellulose was also compared with traditional blocking agents.

Plastic-backed nitrocellulose (Schleicher and Schuell, part #76489, Keene, N.H.) was cut into 1×3 cm pieces. The nitrocellulose was then soaked briefly in 50% ethanol by immersing one end and pulling through the ethanol solution.

The sheets were washed three times briefly in water and then soaked with shaking in 2 × SSC for 5 minutes. 100 ng of lamba-double strand DNA was spotted at 300 micron intervals. The DNA was irreversibly immobilized by UV irradiation (120,000 microjoules/$cm^2$ over a 30 second period). To denature the dsDNA, the sheets were wetted with 50% EtOH, and then washed 2× with water. The sheets were then soaked in denaturation solution (0.1 N NaOH, 0.05 mM EDTA) at room temperature for 1 minute, rinsed quickly with water, washed three times briefly in neutralization solution (0.1 M Tris pH 7.2, 0.05 mM EDTA), washed once in water and the sheets patted dry with paper towels. The DNA was again treated with UV irradiation (120,000 microjoules/$cm^2$ over a 30 second period). The sheets were rehydrated with 50% ethanol for 5 minutes, and washed twice with water.

The sheets were then split into 5 containers for separate "blocking" procedures. Each container confined the nitrocellulose sheets that were blocked with the chemical agents propionic anhydride, butyric anhydride, difluorophthalic anhydride or succinic anhydride. To block the sheets with either propionic anhydride, butyric anhydride, difluorophthalic anhydride, or succinic anhydride, the respective compound was dissolved in 25 ml m-pyrol to a final concentration of 1 molar. An equal volume of 0.1 M NaBorate pH 8.5 was then added. The solution was mixed well and then added to the sheets. Incubation with gentle mixing was for 10 minutes. The sheets were then washed 5 times with 0.01 M Tris, and 0.005 EDTA. The sheet in the fifth container were blocked with 5× Denhardt's solution. This was prepared by placing 10 ml of 50× stock of Dehardt's solution (5 grams Ficoll (type 400, Pharmacia), 5 grams polyvinylpyrrolidone, 5 grams bovine serum albumin (Fraction 5, Sigma) and water to 500 ml total volume) into 90 ml water and adding fragmented single strand herring sperm DNA to a final concentration of 100 micrograrns/ml. The solution was mixed well and then added to sheets. Incubation was by mixing for 30 minutes. The sheets were then washed 5 times with 0.01 M Tris pH, and 0.005 EDTA.

Biotinylated oligonucleotide (DMO 469; SEQ ID NO: 1 (GTTTAACATACTTTCATTT)) was added to a final concentration of 10 ng/ml in 1000 μl of rapid hybridization solution (Rapid-Hyb, Amersham, Arlington Heights, Ill.). The hybridizations were heated to 42° C. for 60 minutes. The sheets were then rinsed four times with 1× SSSC/0.1% SDS for 1 minute each wash. The sheets were then washed 2× with Wash Solution (0.01 M Tris pH 7.2, 0.1 M NaCl, 0.005 M EDTA, 0.1% Sarkosyl).

The streptavidin/HRP conjugate (Vector, Burlingame, Calif.) was diluted (1:2,000) with wash solution. The solution was then applied to sheet for 1 hour at room temperature with shaking. The sheets were then rinsed four times with wash solution, rinsed once with phosphate buffered saline (PBS) for 5 minutes. The HRP substrate was prepared by placing 25 mg of 4-methoxy-napthol in 7.5 ml of MeOH which in turn was added to 42.5 ml PBS containing 33 μl 30% hydrogen peroxide. The reaction was carried out for 15 minutes at room temperature. The sheets were then rinsed with water 5 times and dried.

The results indicated a significant lower level of "background" color on the sheets treated with one of the anhydrides compared to the sheets blocked with Denhardt's reagent.

| Type of blocking step: | Relative color of background (Scale 1–10) |
|---|---|
| Propionic anhydride | 2 |
| Butyric anhydride | 2 |
| Difluorophthalic anhydride | 3 |
| Succinic Anhydride | 1 |
| Denhardt's | 7 |

The scale of the background is on a scale of 1 to 10 with 1 being the lightest color intensity and 10 being the darkest or most intense background. The results indicate that the background is substantially reduced when the nitrocellulose sheets are chemically blocked with any of the 4 types of anhydrides compared to Denhardt's blocking. Although propionic anhydride, butyric anhydride, and difluorophthalic anhydride are not as effective as succinic anhydride, they are an improvement over Denhardt's solution.

Example 6

Demonstration of the Reduction of Background with Propionic Anhydride, Butyric Anhydride, Difluorophthalic Anhydride Blocked Glass Slides Compared to the Denhardt's Blocked Slides Using A Colorimetric Reporter In this example, three types of anhydrides were compared using a non-porous solid support (glass slides). To compare the type of anhydrides, oligonucleotides were covalently immobilized to the slides using a cross-linking reagent, and probed with a complementary biotinylated oligonucleotide. The hybridized signal oligonucleotide was then detected with streptavidin/horseradish peroxidase (SA/HRP) using a colorimetric substrate (4-methoxy-napthol, 4 MN). The chemical means of blocking the glass slides were also compared with traditional blocking agents (Denhardt's solution).

The slides (Sectionlock™, purchased from Polysciences, Warrington, Pa.) were washed three times in water and then incubated for 4 hours in 2× SSC. 100 ng of lamba-double strand DNA was spotted onto the slide using a micropipettor. The DNA was irreversibly immobilized by UV irradiation (120,000 microjoules/$cm^2$ over a 30 second period). To denature the dsDNA, the slides were then soaked in denaturation solution (0.1 N NaOH, 0.05 mM EDTA at room temperature for 1 minute, rinsed quickly with water, and washed three times briefly in neutralization solution (0.1 M Tris pH 7.2, 0.05 mM EDTA).

The slides were then split into 5 containers for separate "blocking" procedures. Each container contained a slide that was blocked with one of the following chemical agents: propionic anhydride, butyric anhydride, difluorophthalic anhydride or succinic anhydride. To block the slides with either propionic anhydride, butyric anhydride, difluorophthalic anhydride, or succinic anhydride, the respective compound was dissolved in 25 ml m-pyrol to a final concentration of 1 molar. An equal volume of 0.1 M NaBorate pH 8.5 was then added. The solution was mixed well and then added to the slides. Incubation with gentle mixing was for 10 minutes. The slides were then washed twice with 100% m-pyrol and then 5 times with 0.01 M Tris, and 0.005 EDTA. The slides in the fifth container were blocked with 5× Denhardt's solution. This was prepared by placing 10 ml of 50× stock of Denhardt's solution (5 grams Ficoll (type 400, Pharmacia), 5 grams polyvinylpyrrolidone, 5 grams bovine serum albumin (Fraction 5, Sigma) and water to 500 ml total volume) into 90 ml water and adding fragmented single strand herring sperm DNA to a final concentration of 100 micrograms/ml. The solution was mixed well and then added to slides. Incubation was by gentle mixing for 30 minutes. The slides were then washed 5 times with 0.01 M Tris pH, and 0.005 EDTA.

Biotinylated oligonucleotide (DMO 469; SEQ ID NO: 1 (GTTTAACATACTTTCATTT)) was added to a final concentration of 10 ng/ml in 1000 μl of rapid hybridization solution (Rapid-Hyb, Amersham, Arlington Heights, Ill.). The hybridizations were conducted at 42° C. for 60 minutes. The slides were then rinsed four times with 1× SSC/0.1% SDS for 1 minute each wash. The slides were then washed 2× with Wash Solution (0.01 M Tris pH 7.2, 0.1 M NaCl, 0.005 M EDTA, 0.1% Sarkosyl).

The streptavidin/HRP conjugate (Vector, Burlingame, Calif.) was diluted (1:2.000) with wash solution. The solution was then applied to each set of slides for 1 hour at room temperature with shaking. The slides were then rinsed four times with wash solution, and rinsed once with phosphate buffered saline (PBS) for 5 minutes. The HRP substrate was prepared by placing 25 mg of 4-methoxy-napthol in 7.5 ml of MeOH which in turn was added to 42.5 ml PBS containing 33 μl 30% hydrogen peroxide. The reaction was carried out for 15 minutes at room temperature. The slides were then rinsed with water 5 times and dried.

The results indicated a significant lower level of "background" color on the slides treated with one of the anhydrides compared to the slide blocked with Denhardt's reagent.

| Type of blocking step: | Relative color of background (Scale 1–10) |
| --- | --- |
| Propionic anhydride | 1 |
| Butyric anhydride | 2 |
| Difluorophthalic anhydride | 2 |
| Succinic Anhydride | 1 |
| Denhardt's | 4 |

The scale of the background is on a scale of 1 to 10 with 1 being the lightest color intensity and 10 being the darkest or most intense background. The results indicate that the background is substantially reduced when the commercially available slides are chemically blocked with any of the 4 types of anhydrides compared to Denhardt's blocking. Although butyric anhydride and difluorophthalic anhydride are not as effective as the propionic anhydride or succinic anhydride, they are an improvement over Denhardt's solution.

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

I claim:

1. A method for reducing non-specific background in binding reactions on solid supports, comprising the steps of:

(a) contacting a solid support with a target ligand under conditions sufficient to immobilize said target ligand to said solid support, wherein said target ligand is a nucleic acid free of protein;

(b) reacting said solid support containing immobilized target ligand with a compound under conditions sufficient to block non-specific sites on said solid support, thereby producing a blocked solid support containing immobilized target ligand, said compound having the formula:

(I)

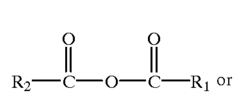

or (II)

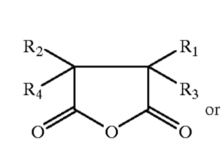

or (III)

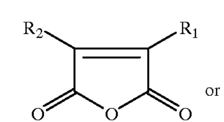

or

-continued (IV)

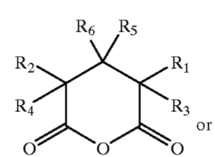

or (V)

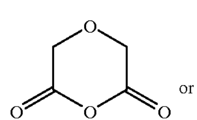

or (VI)

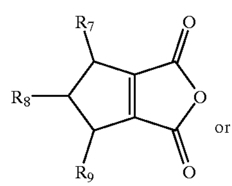

or (VII)

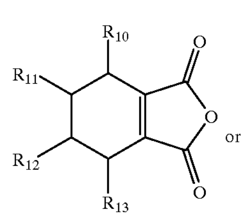

or (VIII)

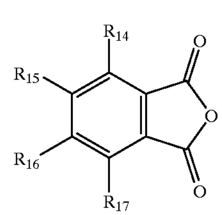

wherein $R_1$–$R_{17}$ are independently selected from H, OH, $CH_3$, $CH_2—CH_3$, $CH═CH—CH_3$, X, $CH_2X$, $CHX_2$, $CH_2—CH_2X$, $CH_2—CHX_2$, $CX_3$, $CX_2—CX_3$, $CX_2—CX_2—CX_3$ and $C(═O)CH_3$, and $R_1$ and $R_3$, or $R_2$ and $R_4$, or $R_5$ and $R_6$ may be taken together as $═CH_2$, and $R_5$ and $R_6$ may be taken together as ═O, and where each X is independently selected from halogen;

(c) contacting said blocked solid support containing immobilized target ligand with a probe under conditions sufficient for specific binding to said immobilized target ligand, wherein said probe is a nucleic acid free of protein; and (d) detecting the presence of said probe on said solid support, thereby determining binding between said target ligand and said probe.

2. The method of claim 1 additionally including, between steps (b) and (c), a step comprising eliminating substantially all of said compound that has not reacted with said blocked solid support containing immobilized target ligand.

3. The method of claim 1 additionally including, between steps (c) and (d), a step comprising eliminating substantially all of said probe that has not bound to said immobilized target ligand.

4. The method of claim 1 additionally including, between steps (b) and (c), a step comprising eliminating substantially all of said compound that has not reacted with said blocked solid support containing immobilized target ligand, and additionally including, between steps (c) and (d), a step comprising eliminating substantially all of said probe that has not bound to said immobilized target ligand.

5. A method for preparing solid supports that reduces non-specific background in binding reactions, comprising the steps of:

(a) contacting a solid support with a target ligand under conditions sufficient to immobilize said target ligand to said solid support, wherein said target ligand is a nucleic acid free of protein; and (b) reacting said solid support containing immobilized target ligand with a compound under conditions sufficient to block non-specific sites on said solid support, thereby producing a blocked solid support containing immobilized target ligand, said compound having the formula:

(I)

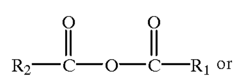

or (II)

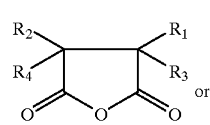

or (III)

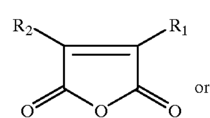

or (IV)

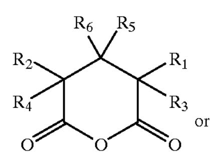

or (V)

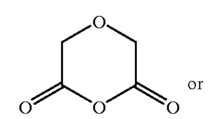

or (VI)

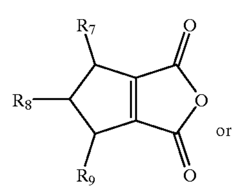

or (VII)

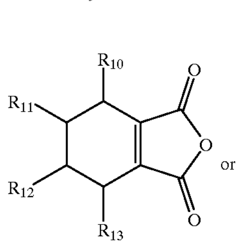

or

-continued (VIII)

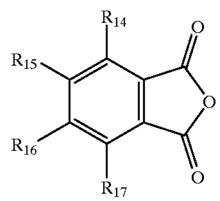

wherein $R_1$–$R_{17}$ are independently selected from H, OH, $CH_3$, $CH_2$—$CH_3$, CH═CH—$CH_3$, X, $CH_2X$, $CHX_2$, $CH_2$—$CH_2X$, $CH_2$—$CHX_2$, $CX_3$, $CX_2$—$CX_3$, $CX_2$—$CX_2$—$CX_3$ and C(═O)$CH_3$, and $R_1$ and $R_3$, or $R_2$ and $R_4$, or $R_5$ and $R_6$ may be taken together as ═$CH_2$, and $R_5$ and $R_6$ may be taken together as ═O, and where each X is independently selected from halogen.

6. The method of claim 5 additionally including, after step (b), a step comprising eliminating substantially all of said compound that has not reacted with said blocked solid support containing immobilized target ligand.

7. The method of any one of claims 1, 2, 3, 4, 5 or 6 wherein said solid support is a nitrocellulose membrane, a nylon membrane or a glass surface.

8. The method of claim 7 wherein said solid support is a nitrocellulose membrane or a nylon membrane.

9. The method of any one of claims 1–6 wherein the compound is according to formula I where $R_1$ and $R_2$ are both CH═CH—$CH_3$ or $CH_2X$ or $CX_3$ or $CX_2$—$CX_3$ or $CX_2$—$CX_2$—$CX_3$, with each X independently selected from halogen.

10. The method of any one of claims 1–6 wherein the compound is according to formula II where $R_1$–$R_4$ are H; or $R_1$ is $CH_3$ and $R_2$–$R_4$ are H; or $R_2$ and $R_4$ are H and $R_1$ and $R_3$ are taken together as ═$CH_2$; or $R_1$ and $R_2$ are H and $R_3$ and $R_4$ are C(═O)$CH_3$.

11. The method of any one of claims 1–6 wherein the compound is according to formula III where $R_1$–$R_4$ are H; or $R_1$ is $CH_3$ and $R_2$ is H; or $R_1$ and $R_2$ are $CH_3$; or $R_1$ is X and $R_2$ is H; or $R_1$ and $R_2$ are X; with each X independently selected from halogen.

12. The method of any one of claims 1–6 wherein the compound is according to formula IV where $R_1$–$R_6$ are H; or $R_1$–$R_5$ are H and $R_6$ is $CH_3$; or $R_1$ and $R_3$ are $CH_3$ and $R_2$, $R_4$, $R_5$ and $R_6$ are H; or $R_1$–$R_4$ are H and $R_5$ and $R_6$ are $CH_3$; or $R_1$–$R_4$ are H and $R_5$ is $CH_3$ and $R_6$ is $CH_2CH_3$; or $R_1$–$R_6$ are X; or $R_1$ and $R_2$ are H and $R_3$ and $R_4$ are C(═O)$CH_3$ and $R_5$ and $R_6$ are taken together as ═O.

13. The method of any one of claims 1–6 wherein the compound is according to formula VI where $R_7$–$R_9$ are H.

14. The method of any one of claims 1–6 wherein the compound is according to formula VII where $R_{10}$–$R_{13}$ are H.

15. The method of any one of claims 1–6 wherein the compound is according to formula VIII where $R_{14}$ and $R_{17}$ are X and $R_{15}$ and $R_{16}$ are H; or $R_{14}$–$R_{17}$ are X; or $R_{14}$ is OH and $R_{15}$–$R_{17}$ are H.

16. A kit comprising a solid support prepared according to a method of either claim 5 or 6.

17. The method of claim 7 wherein the compound is according to formula I where $R_1$ and $R_2$ are both CH═CH—$CH_3$ or $CH_2X$ or $CX_3$ or $CX_2$—$CX_3$ or $CX_2$—$CX_2$—$CX_3$with each X independently selected from halogen.

18. The method of claim 8 wherein the compound is according to formula I where $R_1$ and $R_2$ are both CH═CH—$CH_3$ or $CH_2X$ or $CX_3$ or $CX_2$—$CX_3$ or $CX_2$—$CX_2$—$CX_3$, with each X independently selected from halogen.

19. The method of claim 7 wherein the compound is according to formula II where $R_1$–$R_4$ are H; or $R_1$ is $CH_3$ and $R_2$–$R_4$ are H; or $R_2$ and $R_4$ are H and $R_1$ and $R_3$ are taken together as ═$CH_2$; or $R_1$ and $R_2$ are H and $R_3$ and $R_4$ are C(═O)$CH_3$.

20. The method of claim 8 wherein the compound is according to formula II where $R_1$–$R_4$ are H; or $R_1$ is $CH_3$ and $R_2$–$R_4$ are H; or $R_2$ and $R_4$ are H and $R_1$ and $R_3$ are taken together as ═$CH_2$; or $R_1$ and $R_2$ are H and $R_3$ and $R_4$ are C(═O)$C_3$.

21. The method of claim 7 wherein the compound is according to formula III where $R_1$–$R_4$ are H; or $R_1$ is $CH_3$ and $R_2$ is H; or $R_1$ and $R_2$ are $CH_3$; or $R_1$ is X and $R_2$ is H; or $R_1$ and $R_2$ are X; with each X independently selected from halogen.

22. The method of claim 8 wherein the compound is according to formula III where $R_1$–$R_4$ are H; or $R_1$ is $CH_3$ and $R_2$ is H; or $R_1$ and $R_2$ are $CH_3$; or $R_1$ is X and $R_2$ is H; or $R_1$ and $R_2$ are X; with each X independently selected from halogen.

23. The method of claim 7 wherein the compound is according to formula IV where $R_1$–$R_6$ are H; or $R_1$–$R_5$ are H and $R_6$ is $CH_3$; or $R_1$ and $R_3$ are $CH_3$ and $R_2$, $R_4$, $R_5$ and $R_6$ are H; or $R_1$–$R_4$ are H and $R_5$ and $R_6$ are $CH_3$; or $R_1$–$R_4$ are H and $R_5$ is $CH_3$ and $R_6$ is $CH_2CH_3$; or $R_1$–$R_6$ are X; or $R_1$ and $R_2$ are H and $R_3$ and $R_4$ are C(═O)$CH_3$ and $R_5$ and $R_6$ are taken together as ═O.

24. The method of claim 8 wherein the compound is according to formula IV where $R_1$–$R_6$ are H; or $R_1$–$R_5$ are H and $R_6$ is $CH_3$; or $R_1$ and $R_3$ are $CH_3$ and $R_2$, $R_4$, $R_5$ and $R_6$ are H; or $R_1$–$R_4$ are H and $R_5$ and $R_6$ are $CH_3$; or $R_1$–$R_4$ are H and $R_5$ is $CH_3$ and $R_6$ is $CH_2CH_3$; or $R_1$–$R_6$ are X; or $R_1$ and $R_2$ are H and $R_3$ and $R_4$ are C(═O)$CH_3$ and $R_5$ and $R_6$ are taken together as ═O.

25. The method of claim 7 wherein the compound is according to formula VI where $R_7$–$R_9$ are H.

26. The method of claim 8 wherein the compound is according to formula VI where $R_7$–$R_9$ are H.

27. The method of claim 7 wherein the compound is according to formula VII where $R_{10}$–$R_{13}$ are H.

28. The method of claim 8 wherein the compound is according to formula VII where $R_{10}$–$R_{13}$ are H.

29. The method of claim 7 wherein the compound is according to formula VIII where $R_{14}$ and $R_{17}$ are X and $R_{15}$ and $R_{16}$ are H; or $R_{14}$–$R_{17}$ are X; or $R_{14}$ is OH and $R_{15}$–$R_{17}$ are H.

30. The method of claim 8 wherein the compound is according to formula VIII where $R_{14}$ and $R_{17}$ are X and $R_{15}$ and $R_{16}$ are H; or $R_{14}$–$R_{17}$ are X; or $R_{14}$ is OH and $R_{15}$–$R_{17}$ are H.

31. The method of any one of claims 1–6 wherein the compound is according to formula II where $R_1$–$R_4$ are H.

32. The method of claim 7 wherein the compound is according to formula II where $R_1$–$R_4$ are H.

33. The method of claim 8 wherein the compound is according to formula II where $R_1$–$R_4$ are H.

* * * * *

```
                         SEQUENCE LISTING

(1) GENERAL INFORMATION:

   (iii) NUMBER OF SEQUENCES: 1

(2) INFORMATION FOR SEQ ID NO:1:

     (i) SEQUENCE CHARACTERISTICS:
          (A) LENGTH: 19 base pairs
          (B) TYPE: nucleic acid
          (C) STRANDEDNESS: single
          (D) TOPOLOGY: linear

    (xi) SEQUENCE DESCRIPTION: SEQ ID NO:1:

GTTTAACATA CTTTCATTT                                              19
```